United States Patent
Peterson et al.

(10) Patent No.: US 6,200,606 B1
(45) Date of Patent: Mar. 13, 2001

(54) ISOLATION OF PRECURSOR CELLS FROM HEMATOPOIETIC AND NONHEMATOPOIETIC TISSUES AND THEIR USE IN VIVO BONE AND CARTILAGE REGENERATION

(75) Inventors: Dale R. Peterson, Carmel; Nancy Nousek-Goebl, Fishers, both of IN (US)

(73) Assignee: DePuy Orthopaedics, Inc., Warsaw, IN (US)

(*) Notice: Subject to any disclaimer, the term of this patent is extended or adjusted under 35 U.S.C. 154(b) by 0 days.

(21) Appl. No.: 08/891,952

(22) Filed: Jul. 14, 1997

Related U.S. Application Data

(63) Continuation-in-part of application No. 08/587,315, filed on Jan. 16, 1996.

(51) Int. Cl.$^7$ ............................................. A61K 35/12
(52) U.S. Cl. ..................... 424/574; 424/93.7; 424/93.71
(58) Field of Search .............................. 424/93.7, 93.71, 424/529, 577, 574; 435/372

(56) References Cited

U.S. PATENT DOCUMENTS

| | | | |
|---|---|---|---|
| 4,609,551 | 9/1986 | Caplan et al. | 424/549 |
| 4,820,626 | 4/1989 | Williams et al. | 435/1.1 |
| 5,081,030 | * 1/1992 | Civin | 435/240.2 |
| 5,197,985 | 3/1993 | Caplan et al. | 128/898 |
| 5,226,914 | 7/1993 | Caplan et al. | 435/325 |
| 5,230,693 | 7/1993 | Williams et al. | 623/1.41 |
| 5,294,446 | 3/1994 | Schlameus et al. | 424/489 |
| 5,411,885 | 5/1995 | Marx et al. | 435/402 |
| 5,672,346 | * 9/1997 | Srour et al. | 424/93.7 |
| 5,716,616 | 2/1998 | Prockop et al. | 424/93.7 |
| 5,837,235 | * 11/1998 | Mueller et al. | 424/93.7 |

FOREIGN PATENT DOCUMENTS

| | | |
|---|---|---|
| 0 333 328 A2 | 9/1989 | (EP) . |
| WO 92/22584 | 12/1992 | (WO) . |
| WO 94/09722 | 5/1994 | (WO) . |

OTHER PUBLICATIONS

Rockard et al., "Isolation of Precursor Cells from Human Bone Marrow that can Differentiate into Osteoblasts and Adipocytes", Journal of Bone and Mineral Research, vol. 10, Supplement 1, p. S422, see entire abstract, Aug. 1995.
Joyner et al., "Identification and Enrichment of Human Osteoprogenitor Cells By Using Differentiation Stage–Specific Monoclonal Antibodies", Bone, vol. 21, No. 1, pp. 1–6, Jul. 1997.
Bosse, Alexander, "Clinical Aspects, Differential Diagnosis and Histogenesis of Heterotopic Ossification", Gustav Fischer, vol. 146, Oct. 1996.
Terstappen et al., Blood Cells 20: 45–63 (1994).
Simmons et al., Blood 78(11): 2848–2853 (Dec. 1, 1991).
"Determined and inducible osteogenic precursor cells", Friedenstein, Symposium on Hard Tissue Growth, Repair and Remineralization, Ciba Foundation Symposium 11, pp. 169–185, 1973.
"Expression of Human Bone–related Proteins in the Hematopoietic Microenvironment", Long et al., Journal of Clinical Investigation, vol. 86, pp. 1387–1395, Nov. 1990.
"Formation of Bone Tissue in Culture From Isolated Bone Cells", Binderman et al., The Journal of Cell Biology, vol. 61, pp. 427–439, 1974.
"Marrow Stromal Fibroblasts", Friedenstein, Calcified Tissue International, 56 (Suppl. 1):517, 1995.
"Stromal stem cells: marrow–derived osteogenic precursors", Owen et al., Cell and Molecular Biology of Vertebrate Hard Tissues. Ciba Foundation Symposium 136, pp. 42–60, 1988.
"The Development of Fibroblast Colonies in Monolayer Cultures of Guinea–Pig Bone Marrow and Spleen Cells", Friedenstein et al., Cell Tissue Kinet.(3), pp. 393–403, 1970.
"The Osteogenic Potential of Marrow", Maureen Owen, Development and Diseases of Cartilage and Bone Matrix, pp. 247–255, 1987.
"Bone Morphogenetic Proteins, Bone Marrow Stromal Cells, and Mesenchymal Stem Cells", A.H. Reddi, Clinical Orthopaedics and Related Research, No. 313, pp. 115–119, 1995.
"Osteogenesis in transplants of bone marrow cells", Friedenstein et al., J. Embryol. Exp. Morph., vol. 16(3), pp. 581–390, Dec. 1966.
"Stromal–Hematopoietic Interrelationships: Maximov's Ideas and Modern Models", A. Friedenstein, Symposium on Modern Trends in Human Leukemia VIII, pp. 159–167, Jun. 19–23, 1988.
The STRO–1+ Fraction of Adult Human Bone Marrow Contains the Osteogenic Precursors, A. Friedenstein, Blood, vol. 84, No. 12, pp. 4164–4173, Dec. 15, 1997.
"Isolation and Differentiation of Mesenchymal Stem Cells from Rabbit Muscle", Pate et al,. Proceeding for the 49th Annual Sessions on Fundamental Surgical Problems, vol. XLIV, pp. 587–589, 1993.
"Microvascular Cell Response to Osteoblast–Like Bone Cell Conditioned Media", Jones et al., 39th Annual Meeting, Orthopaedic Research Society, Feb. 15–18, 1993.
"Characterization of a 5–Fluorouracil–Enriched Osteoprogenitor Population of the Murine Bone Marrow", Falla et al., Blood, vol. 82, No. 12, pp. 3580–3591, Dec. 15, 1993.

(List continued on next page.)

Primary Examiner—Jean C. Witz
(74) Attorney, Agent, or Firm—Barnes & Thornburg; Alice O. Martin

(57) ABSTRACT

The present invention relates to the isolation of cartilage or bone precursor cells from hematopoietic and non-hematopoietic cells and their use in bone and cartilage regeneration procedures. The precursor cells are used for in vivo bone or cartilage repair by transplanting the cells, with or without a carrier material and without the need for in vitro culturing of the cells, to sites in the body requiring bone or cartilage repair.

9 Claims, No Drawings

OTHER PUBLICATIONS

"Bone Morphogenetic Protein Expression in Human Atherosclerotic Lesions", Bostrom et al., Journal of Clinical Investigation, vol. 91, pp. 1800–1809, Apr. 1993.

"Binding of L–Selection to the Vascular Sialomucin CD34", Baumhueter et al., Science, vol. 262, pp. 436–438, Oct. 15, 1993.

Lymphoid and Myeloid Differentiation of Single Human CD34+, HLA–DR+, CD38– Hematopoietic Stem Cells, Huang et al., Blood, vol. 83, No. 6, pp. 1515–1526, Mar. 15, 1994.

"Characterization of Cells with Osteogenic Potential from Human Marrow", Haynesworth et al., Bone, 13, pp. 81–88, 1992.

"Rib Perichondrial Autografts in Full–Thickness Articular Cartilage Defects in Rabbits", Coutts et al., Clinical Orthopaedics and Related Research, No. 275, pp. 263–273, Feb. 1992.

"The Pericyte as a Possible Osteoblast Progenitor Cell", Brighton et al., Clinical Orthopaedics and Related Research, No. 275, pp. 287–299, Feb. 1992.

"CD34 Expression by Stromal Precursors in Normal Human Adult Bone Marrow", Simmons et al., Blood, vol. 78, No. 11, pp. 2848–2853, Dec. 1, 1991.

"The Origin of Bone Cells in the Postnatal Organism", Arthritis and Rheumatism, vol. 23, No. 10, pp. 1073–1080, Oct. 1980.

"Osteogenesis in Marrow–Derived Mesenchymal Cell Porous Ceramic Composites Transplanted Subcutaneously: Effect of Fibronectin and Laminin on Cell Retention and Rate of Osteogenic Expression", Dennis et al., Cell Transplantation, vol. 1, No. 1, pp. 23–32, 1992.

"Pericytes as a Supplementary Source of Osteoblasts in Periosteal Osteogenesis", Diaz–Flores et al., Clinical Orthopaedics and Related Research, No. 275, pp. 280–286, Feb. 1992.

"Adipocytic cells cultured from marrow have osteogenic potential", Bennett et al., Journal of Cell Science, pp. 131–139, 1991.

"Mesenchymal Stem Cells", Arnold I. Caplan, Journal of Orthopaedic Research, pp. 641–650, 1991.

"The Osteogenic Potential of Culture–Expanded Rat Marrow Mesenchymal Cells Assayed in Vitro in Calcium Phosphate Ceramic Blocks", Goshima et al., Clinical Orthopaedics and Related Research, No. 262, pp. 289–311, Jan. 1991.

"The Chondrogenic Potential of Free Autogenous Periosteal Grafts for Biological Resurfacing of Major Full–Thickness Defects in Joint Surfaces under the Influence of Continuous Passive Motion", O'Driscoll et al., The Journal of Bone and Joint Surgery, vol. 68–A, No. 7, pp. 1017–1034, Sep. 1986.

"In Vitro Differentiation of Bone and Hypertrophic Cartilage from Periosteal–Derived Cells", Nakahara et al., Experimental Cell Research, 195, pp. 492–503, 1991.

"The Repair of Segmental Bone Defects with Collagen and Marrow", Werntz et al., Orthopaedic Research Society, pp. 262–263, 1986.

"Positive selection of viable cell populations using avidin–biotin immunoadsorption", Berenson et al. Journal of Immunological Methods, 91, pp. 11–19, 1986.

"Osteogenic Stem Cells and the Stromal System of Bone and Marrow", Beresford et al., Clinical Orthopaedics and Related Research, No. 240, pp. 270–280, Mar. 1989.

"Development of an Osteogenic Bone–Marrow Preparation," Connolly et al., The Journal of Bone and Joint Surgery, pp. 684–691, 1989.

"The Role of Cells Versus Matrix in Bone Induction", H. Clarke Anderson, Connective Tissue Research, vol. 24, pp. 3–12, 1990.

"Formation of hematopoietic microenvironment and hematopoietic stem cells from single human bone marrow stem cells", Haung et al., Nature, vol. 360, pp. 745–749, 1992.

"Multi–talented stem cells?", Dexter et al., Nature, vol. 360, p. 709, Dec. 1992.

"Cell Surface Antigens on Human Marrow–Derived Mesenchymal Cells are Detected by Monoclonal Antibodies", Haynesworth et al., Bone, 13, pp. 69–80, 1992.

"Mesenchymal Stem Cells Reside Within the Connective Tissues of Many Organs", Young et al., Developmental Dynamics, 202, pp. 137–144, 1995.

"The "Common Stem Cell" Hypothesis Reevaluated: Human Fetal Bone Marrow Contains Separate Populations of Hematopoietic and Stromal Progenitors", Blood, vol. 85, No. 9, pp. 2422–2435, May 1, 1995.

"A population of cells resident within embryonic and newborn rat skeletal muscle is capable of differentiating into multiple mesodermal phenotypes", Lucas et al., Wound Repair and Regeneration, vol. 3, No. 4, pp. 449–460, Oct.–Dec. 1995.

"Pericytes derived from the retinal microvasculature undergo calcification in vitro", Schor et al., Journal of Cell Science, 97, pp. 446–461, 1990.

"Regulation of Human Bone Marrow–derived Osteoprogenitor Cells by Osteogenic Growth Factors", Long et al., Journal of Clinical Investigation, vol. 95, pp. 881–887, Feb. 1995.

"Expression of CD34 Gene in Vascular Endothelial Cells", Blood, vol. 75, No. 12, pp. 2417–2426, Jun. 15, 1990.

"Characterization of Murine CD34, a Marker for Hematopoietic Progenitor and Stem Cells", Krause et al., Blood, vol. 84, No. 3, pp. 691–701, Aug. 1, 1994.

"Expression and Regulation of Ly–6 Differentiation Antigens of Murine Osteoblasts", Horowitz et al., Endocrinology, vol. 135, No. 3, pp. 1032–1043, 1994.

"Microvessel Endothelial Cells and Pericytes Increase Proliferation and Repress Osteoblast Phenotypic Markers in Rat Calvarial Bone Cell Cultures", Jones et al., Journal of Orthopaedic Research, 13, pp. 553–561, 1995.

"A Hematopoietic Progenitor Cell Surface Antigen Defined by a Monoclonal Antibody Raised against KG–Ia Cells", Civin et al., The Journal of Immunology, vol. 133, No. 1, pp. 157–165, Jul. 1984.

"Mesenchymal Cell–Based Repair of Large, Full–Thickness Defects of Articular Cartilage", Wakitani et al., The Journal of Bone and Joint Surgery, vol. 76, No. 4, pp. 579–592, Apr. 1994.

"Analysis of Bone Marrow Stem Cell", Terstappen et al., Blood Cells, vol. 20, pp. 45–63, 1994.

TGF–$\beta$1 and 25–Hydroxycholesterol Stimulate Osteoblast–ike Vascular Cells to Calcify, Watson et al., Journal of Clinical Investigation, vol. 93, pp. 2106–2113, May 1994.

"Osteoblast and Chondroblast Differentiation", Aubin et al., Bone, vol. 17, No. 2, Supplement, pp. 77S–83S, Aug. 1995.

"Repair of Articular Cartilage Defects Using Mesenchymal Stem Cells", Grande et al., Tissue Engineering, vol. 1, No. 4, pp. 345–353, 1995.

"In Vitro Effects of Growth Factors and Dexamethasone on Rat Morrow Stromal Cells", Locklin et al., Clinical Orthopaedics and Related Research, No. 313, pp. 27–35, 1995.

* cited by examiner

ISOLATION OF PRECURSOR CELLS FROM HEMATOPOIETIC AND NONHEMATOPOIETIC TISSUES AND THEIR USE IN VIVO BONE AND CARTILAGE REGENERATION

CROSS REFERENCE TO RELATED APPLICATION

This application is a continuation-in-part of pending U.S. application Ser. No. 08/587,315, filed Jan. 16, 1996.

BACKGROUND OF THE INVENTION

The present invention generally relates to the isolation of precursor cells and their use in bone and cartilage regeneration procedures and, more particularly, is directed to a method for isolating bone/cartilage precursor cells from a variety of body tissue types utilizing cell surface antigen CD34, other precursor cell surface antigens on CD34+ cells, and other positive and negative cell selection techniques.

Osteogenesis and chondrogenesis are highly complex biological processes having considerable medical and clinical relevance. For example, more than 1,400,000 bone grafting procedures are performed in the developed world annually. Most of these procedures are administered following joint replacement surgeries, or during trauma surgical reconstructions. The success or failure of bone grafting procedures depends largely on the vitality of the site of grafting, graft processing, and in the case of allografts, on immunological compatibility between donor and host. Compatibility issues can largely be negated as an important consideration in the case of autologous grafting procedures, which involve taking bone tissue from one site of the patient for transplantation at another site. While autologous bone grafts are generally successful they do require additional surgery in order to harvest the graft material, and not uncommonly are accompanied by post-operative pain, hemorrhage and infection.

Cartilage regeneration and replacement procedures are perhaps even more problematic. Unlike osteogenesis, chondrogenesis does not typically occur to repair damaged cartilage tissue. Attempts to repair damaged cartilage in any clinically meaningful fashion have met with only limited success. In many cases, the most effective treatment for cartilage damage is prosthetic joint replacement.

These and other difficulties with presently available bone-grafting and cartilage regeneration procedures have prompted intensive investigations into the cellular and molecular bases of osteogenesis and chondrogenesis. Some promising research to date has been in the identification and isolation of bone and cartilage precursor cells from marrow and other tissues.

Early investigations into the complexity of bone marrow demonstrated that lethally irradiated animals could be rescued by marrow transplants, suggesting that bone marrow contained a restorative factor having the capacity to regenerate the entire hematopoietic system. More recent experiments have shown that marrow also has the capacity to regenerate bone and other mesenchymal tissue types when implanted in vivo in diffusion chambers. (See e.g. A. Friedenstein et al. "Osteogenesis in transplants of bone marrow cells." J. Embryol. Exp. Morph. 16, 381–390,1960; M. Owen. "The osteogenic potential of marrow." UCLA Symp. on Mol. and Cell. Biol. 46, 247–255, 1987) Results of this nature have led to the conclusion that bone marrow contains one or more populations of pluripotent cells, known as stem cells, having the capacity to differentiate into a wide variety of different cell types of the mesenchymal, hematopoietic, and stromal lineages.

The process of biological differentiation, which underlies the diversity of cell types exhibited by bone marrow, is the general process by which specialized, committed cell types arise from less specialized, primitive cell types. Differentiation may conveniently be thought of as a series of steps along a pathway, in which each step is occupied by a particular cell type potentially having unique genetic and phenotypic characteristics. In the typical course of differentiation a pluripotent stem cell proceeds through one or more intermediate stage cellular divisions, ending ultimately in the appearance of one or more specialized cell types, such as T lymphocytes and osteocytes. The uncommitted cell types which precede the fully differentiated forms, and which may or may not be true stem cells, are defined as precursor cells.

Although the precise signals that trigger differentiation down a particular path are not fully understood, it is clear that a variety of chemotactic, cellular, and other environmental signals come into play. Within the mesenchymal lineage, for example, mesenchymal stem cells (MSC) cultured in vitro can be induced to differentiate into bone or cartilage in vivo and in vitro, depending upon the tissue environment or the culture medium into which the cells are placed. (See e.g. S Wakitani et al. "Mesenchymal cell-based repair of large, full-thickness defects of articular cartilage" J. Bone and Joint Surg, 76-A, 579–592 (1994); J Goshima, V M Goldberg, and Al Caplan, "The osteogenic potential of culture-expanded rat marrow mesenchymal cells assayed in vivo in calcium phosphate ceramic blocks" Clin. Orthop. 262, 298–311 (1991); H Nakahara et al. "In vitro differentiation of bone and hypertrophic cartilage from periosteal-derived cells" Exper. Cell Res. 195, 492–503 (1991)).

Studies of this type have conclusively shown that MSC are a population of cells having the capacity to differentiate into a variety of different cell types including cartilage, bone, tendon, ligament, and other connective tissue types. Remarkably, all distinct mesenchymal tissue types apparently derive from a common progenitor stem cell, viz. MSC. The MSC itself is intimately linked to a trilogy of distinctly differentiating cell types, which include hematopoietic, mesenchymal, and stromal cell lineages. Hematopoietic stem cells (HSC) have the capacity for self-regeneration and for generating all blood cell lineages while stromal stem cells (SSC) have the capacity for self-renewal and for producing the hematopoietic microenvironment.

It is a tantalizing though controversial prospect whether the complex subpopulations of cell types present in marrow (i.e. hematopoietic, mesenchymal, and stromal) are themselves progeny from a common ancestor. The search for ancestral linkages has been challenging for experimentalists. Identifying relatedness among precursor and stem cell populations requires the identification of common cell surface markers, termed "differentiation antigens," many of which appear in a transitory and developmentally-related fashion during the course of differentiation. One group, for example, has reported an ancestral connection among MSC, HSC, and SSC, though later issued a partial retraction (S. Huang & L. Terstappen. "Formation of hematopoietic microenvironment and hematopoietic stem cells from single human bone marrow stem cells" Nature, 360, 745–749, 1992; L. Terstappen & S. Huang. "Analysis of bone marrow stem cell" Blood Cells, 20, 45–63, 1994; E K Waller et al. "The common stem cell hypothesis reevaluated: human fetal bone marrow contains separate populations of hematopoietic and stromal progenitors" Blood, 85, 2422–2435, 1995). However, studies by another group have demonstrated that murine osteoblasts possess differentiation antigens of the Ly-6 family. That finding is significant in the present context because the Ly-6 antigens are also expressed by cells of the murine hematopoietic lineage. (M. C. Horowitz et al. "Expression and regulation of Ly-6 differentiation antigens by murine osteoblasts" Endocrinology, 135, 1032–1043, 1994). Thus, there may indeed be a close lineal relationship between mesenchymal and hematopoietic cell types which has its origin in a common progenitor. A final answer on this question must await further study.

One of the most useful differentiation antigens for following the course of differentiation in human hematopoietic systems is the cell surface antigen known as CD34. CD34 is expressed by about 1% to 5% of normal human adult marrow cells in a developmentally, stage-specific manner (CI Civin et al., "Antigenic analysis of hematopoiesis. A hematopoietic progenitor cell surface antigen defined by a monoclonal antibody raised against KG-1a cells" J.Immunol., 133, 157–165, 1984). CD34+ cells are a mixture of immature blastic cells and a small percentage of mature, lineage-committed cells of the myeloid, erythroid and lymphoid series. Perhaps 1% of CD34+ cells are true HSC with the remaining number being committed to a particular lineage. Results in humans have demonstrated that CD34+ cells isolated from peripheral blood or marrow can reconstitute the entire hematopoietic system for a lifetime. Therefore, CD34 is a marker for HSC and hematopoietic progenitor cells.

While CD34 is widely recognized as a marker for hematopoietic cell types, it has heretofore never been recognized as a reliable marker for precursor cells having osteogenic potential in vivo. On the contrary, the prior art has taught that bone precursor cells are not hematopoietic in origin and that bone precursor cells do not express the hematopoietic cell surface antigen CD34 (M W Long, J L Williams, and K G Mann "Expression of bone-related proteins in the human hematopoietic microenvironment" J. Clin. Invest. 86, 1387–1395, 1990; M W Long et al. "Regulation of human bone marrow-derived osteoprogenitor cells by osteogenic growth factors" J. Clin. Invest. 95, 881–887,1995; S E Haynesworth et al. "Cell surface antigens on human marrow-derived mesenchymal cells are detected by monoclonal antibodies" Bone, 13, 69–80, 1992).

To date, the most common sources of precursor cells having osteogenic potential have been periosteum and marrow. Many researchers use cells isolated from periosteum for in vitro assays (See e.g. I Binderman et al. "Formation of bone tissue in culture from isolated bone cells" J-Cell Nol. 61, 427–439. 1974). The pioneer of the concept of culturing bone marrow to isolate precursor cells for studying bone and cartilage formation is A. J. Friedenstein. He developed a culture method for isolating and expanding cells (CFU-f) from bone marrow which can form bone (A. J. Friedenstein et al. "The development of fibroblast colonies in monolayer cultures of guinea pig bone marrow and spleen cells" Cell Tiss. Kinet. 3, 393–402, 1970). Others have used Friedenstein's culture system extensively to study the origin of osteoblasts (See e.g. M. Owen, "The origin of bone cells in the postnatal organism" Arthr. Rheum. 23, 1073–1080, 1980). Friedenstein showed that CFU-f cells from marrow will form bone, cartilage, and fibrous tissue when implanted, though CFU-f cells cultured from other sources such as thymus, spleen, peripheral blood, and peritoneal fluid will not form bone or cartilage without an added inducing agent. Friedenstein recently discussed the possible clinical utility of CFU-f and pointed out some obstacles that must be overcome, such as the need for culturing for several passages and developing a method for transplanting the cells (A. J. Friedenstein "Marrow stromal fibroblasts" Calcif Tiss. Int. 56(S): S17, 1995).

Similarly, the most common sources of cartilage precursor cells to date have been periosteum, perichondrium, and marrow. Cells isolated from marrow have also been used to produce cartilage in vivo (S. Wakdani et al. "Mesenchymal cell-based repair of large, full-thickness defects of articular cartilage" J. Bone and Joint Surg, 76A, 579–592, 1994). Periosteal and perichondral grafts have also been used as sources of cartilage precursor cells for cartilage repair (S W O'Driscoll et al. "Durability of regenerated articular cartilage produced by free autogenous periosteal grafts in major full-thickness defects in joint surfaces under the influence of continuous passive motion" J. Bone and Joint Surg. 70A, 1017–1035, 1986; R Coutts et al. "Rib perichondral autografts in full-thickness articular defects in rabbits" Clin. Orthop. Rel. Res. 275, 263–273,1992).

In a series of patents, Caplan et al. disclose a method for isolating and amplifying mesenchymal stem cells (MSC) from marrow. (U.S. Pat. Nos. 4,609,551; 5,197,985; and 5,226,914) The Caplan method involves two basic steps: 1) harvesting marrow and 2) amplifying the MSC contained in the harvested marrow by a 2 to 3 week period of in vitro culturing. This method takes advantage of the fact that a particular culture medium favors the attachment and propagation of MSC over other cell types. In a variation on this basic method, MSC are first selected from bone marrow using specific antibodies against MSC prior to in vitro culturing. (Caplan and Haynesworth; WO 92/22584) The in vitro amplified, marrow-isolated MSC may then be introduced into a recipient at a transplantation repair site. (A. Caplan. "precursor cells" J. Ortho. Res. 9, 641, 1991; S. E. Haynesworth, M. A. Baber, and A. L. Caplan. "Cell surface antigens on human marrow-derived mesenchymal cells are detected by monoclonal antibodies," Bone, 13, 69–80, 1992).

The current methods used to isolate precursor cells have a number of drawbacks to consider. First, the methods require that bone marrow or other tissues be harvested. Harvesting bone marrow requires an additional surgical procedure with the appendant possibility of complications from anesthesia, hemorrhage, infection, and post-operative pain. Harvesting periosteum or perichondrium is even more invasive. Second, the Caplan method requires a substantial period of time (2 to 3 weeks) for in vitro culturing of marrow-harvested MSC before the cells can be used in further applications. This additional cell culturing step renders the method time-consuming, costly, and subject to more chance for human error.

Consequently, a need exists for a quicker and simpler method for identifying and isolating precursor cells having osteogenic and chondrogenic potential which can be used for in vivo bone and cartilage regeneration procedures.

SUMMARY OF THE INVENTION

The present invention is directed to providing a method for isolating precursor cells having the potential to generate bone or cartilage from a variety of hematopoietic and non-hematopoietic tissues. In one embodiment a method for isolating precursor cells having the potential to generate bone or cartilage is provided. The precursor cells are isolated from peripheral blood, marrow, or adipose tissue based on binding by a reagent to cell surface antigen CD34 or other surface antigens on CD34+ cells.

In another embodiment, a method for isolating bone or cartilage precursor cells from adipose tissue is provided that utilizes sedimentation density differences in the cells comprising the adipose tissue to isolate the precursor cells.

The present invention also provides a method for in vivo bone and cartilage regeneration involving transplantation with CD34+ precursor cells isolated from peripheral blood, marrow, or adipose tissue. In one embodiment, a direct, single-step method for in vivo bone or cartilage regeneration is provided that involves the isolation of CD34+ precursor cells from peripheral blood, marrow, or adipose tissue and immediate implantation at a connective tissue site needing repair without the need for in vitro culturing of precursor cells.

In another embodiment of the present invention a method for enhancing the implantability of bone prosthetic devices is described. The present invention describes an improved bone implantation prosthetic device in which the device is seeded with precursor cells having osteogenic potential isolated from a patient's peripheral blood, bone marrow, or adipose tissue.

The ability to isolate autologous precursor cells having osteogenic and chondrogenic potential has far reaching clinical implications for bone and cartilage repair therapies, either alone or in conjunction with prosthetic devices. The present invention provides a simple method for isolating precursor cells having the potential to generate bone or cartilage from a variety of tissue types including peripheral blood, marrow, and adipose tissue. The precursor cells can be isolated using reagents that recognize CD34 or other markers on the surface of CD34+ precursor cells, for example CD33, CD38, CD74, and THY1. Alternatively, precursor cells or precursor cell enriched cell populations can be isolated by negative selection techniques adapted to separate precursor cells from non-precursor cells. Where adipose tissue is used as the source of precursor cells, a cell population enriched in precursor cells can be separated using sedimentation/density differential based techniques. Significantly, the present invention does not require in vitro culturing of isolated precursor cells before the cells can be used in further in vivo procedures. Indeed, precursor cells isolated by the present invention may be transplanted in vivo immediately for bone or cartilage regeneration. Thus, the 2 to 3 week time delay required by other methods for in vitro culturing of progenitor cells is eliminated making the method economical, practical and useful for the clinical environment.

Accordingly, the present invention relates to a method for isolating precursor cells having the potential to generate bone or cartilage directly from hematopoietic and non-hematopoietic tissues, including peripheral blood. In one preferred embodiment the method includes steps of collecting tissue samples, contacting the sample with an antibody or other reagent that recognizes antigen CD34 or other antigens on CD34+ precursor cells, and separating the reagent-precursor cell complex from unbound material, by for example, affinity chromatography. Precursor cells isolated by the present method may be used immediately for bone and cartilage regeneration in vivo.

In one aspect, the present invention is a method for isolating precursor cells having the potential to generate bone or cartilage from peripheral blood, marrow or adipose tissue.

In another aspect, the present invention is directed to a method for isolating precursor cells having the potential to generate bone or cartilage based on selecting cells from hematopoietic and non-hematopoietic tissues that carry cell surface marker CD34.

In yet another aspect, the present invention is directed to a method for bone or cartilage regeneration which utilizes CD34+ precursor cells isolated from peripheral blood, marrow, or adipose tissue.

DESCRIPTION OF THE PREFERRED EMBODIMENT(S)

Terms used throughout this disclosure are defined as follows:

Adipose Tissue

A complex tissue containing multiple cell types including adipocytes and microvascular cells. Adipose tissue is one of the most convenient sources of precursor cells in the body. As used herein the term "adipose tissue" is intended to mean fat and other sources of microvascular tissue in the body such as placenta or muscle. The term specifically excludes connective tissues, hematologic tissues, periosteum, and perichondrium.

Chondrogenic

The capacity to promote cartilage growth. This term is applied to cells which stimulate cartilage growth, such as chondrocytes, and to cells which themselves differentiate into chondrocytes. The term also applies to certain bioactive compounds, such as TGF-$\beta$, which promote cartilage growth.

Connective Tissue

Any of a number of structural tissues in the body including bone, cartilage, ligament, tendon, meniscus, and joint capsule.

Differentiation

A biological process in which primitive, unspecialized, cells undergo a series of cellular divisions, giving rise to progeny having more specialized functions. The pathway to terminal differentiation ends with a highly specialized cell having unique genetic and phenotypic characteristics. The conventional wisdom of the past taught that differentiation proceeded in one direction only—from less specialized to more specialized. This dogma is now being challenged by new results which suggest that in fact the pathway may be bidirectional. Under certain conditions more specialized cells may in fact produce progeny which effectively reverse the flow toward greater specialization.

Hematopoietic Stem Cell

Primitive cell having the capacity to self-renew and to differentiate into all blood cell types.

Mesenchymal Stem Cell

Primitive cell type having the capacity for self-regeneration and for differentiating through a series of separate lineages to produce progeny cells having a wide variety of different phenotypes, including bone, cartilage, tendon, ligament, marrow stroma, adipocytes, dermis, muscle, and connective tissue.

Microvascular Cell

Cells comprising the structure of the microvasculature such as endothelial, smooth muscle, and pericytes.

Osteogenic

The capacity to promote or to generate the production of bone. The term may be applied to osteoblasts which have the capacity to promote bone growth, or to cells which themselves are able to differentiate into osteoblasts. The term would also apply to growth factors having the capacity to promote bone growth.

Precursor Cell

A cell with the potential to differentiate to perform a specific function.

Stem Cell

Pluripotent precursor cell having the ability to self-renew and to generate a variety of differentiated cell types.

The present invention is premised upon two surprising discoveries. First, that precursor cells having the potential to form connective tissue in vivo can be isolated from a variety of hematopoietic and non-hematopoietic tissue sources, including peripheral blood, and adipose tissue. And second, that cell surface marker CD34, a heretofore unrecognized identifier for connective tissue precursor cells, may be used as a marker for precursor cells having the potential to form bone and cartilage in vivo.

The inventors have discovered two convenient, new sources for precursor cells (viz. peripheral blood and adipose tissue), and a population of cells isolated from marrow which do not require in vitro culture to induce repair of bone or cartilage upon implantation into a host. Unlike prior methods, which have used bone marrow or periosteum as the source for osteogenic and chondrogenic precursor cells, the present invention enables isolation of these cells from more conveniently harvested tissues, such as peripheral blood and adipose tissue. The ability to isolate osteogenic and chondrogenic precursor cells from tissues other than marrow and periosteum lends considerable convenience and simplicity to an otherwise complicated method.

In one embodiment, the present invention is an affinity method enabling the isolation of precursor cells in humans having the potential to generate connective tissue based on expression of antigen CD34 and other cell surface markers on CD34+ cells. Some examples of other markers on CD34+ cells would include CD33, CD38, CD74, and THY1, which list is not intended to be exclusive. In another embodiment, precursor cells are isolated from adipose tissue based on differential sedimentation properties. Advantageously, adipose tissue can be dissociated into a suspension of cells and the fat cells can be separated from precursor cells based on the higher density of the precursor cells (i.e. greater than 1.0 g/cm$^3$) relative to the density of fat cells (i.e. less than or equal to 1.0 g/cm$^3$) and other undesirable cells and cell components. Significantly, unlike previous described methods, the present invention enables the immediate use of isolated precursor cells for bone and cartilage regeneration procedures without the need for in vitro culturing. As a consequence, the present method is quicker and easier to implement than previously described procedures.

I. Isolating Precursor Cells

In one embodiment, the present method for isolating precursor cells involves collecting a body tissue sample, contacting the sample with an antibody or other reagent that recognizes and binds to an antigen on the surface of the precursor cells, and then separating the precursor cell-reagent complex from unbound material by, for example, affinity chromatography. The method can be applied to peripheral blood, marrow, or other tissues, including adipose tissue. For ease and simplicity of isolation, however, blood is the preferred source material since surgical procedures are not required.

(a) Peripheral Blood as the Source of Precursor Cells

By way of example, about 1 unit of blood is taken by any suitable means, for example by venipuncture. A particularly attractive method in the clinical environment is apheresis, which has the added advantage of removing red cells. Removal of red cells is not essential, although it does enhance the performance of the method and is preferred. Red cells may be removed from the sample by any suitable means, for example, lysis, centrifugation, or density gradient separation. It is preferred that the sample also be anticoagulated by, for example, treatment with citrate, heparin, or EDTA.

The yield of precursor cells is expected to be about 0.1% to 0.5% of the population of nucleated blood cells. Yields may vary, depending upon the health and age of the donor, and on the freshness of the sample. The yield may be dramatically increased by administering drugs or growth factors to the patient before blood collection. Although the method will work on samples which have been stored under refrigeration, fresh samples are preferred.

A critical step in a positive selection procedure for isolating precursor cells from peripheral blood involves contacting the blood sample with a reagent that recognizes and binds to a cell surface marker on CD34+ cells. Any reagent which recognizes and binds to CD34+ cells is within the scope of the invention. Suitable reagents include lectins, for example, soy bean agglutinin (SBA), and L-selectin.

In one preferred embodiment the sample is contacted with an antibody against CD34. Either monoclonal (mAb) of polyclonal antibodies may be used. Methods for preparing antibodies directed against CD34 and other cell surface antigens on CD34+ cells are well known to those skilled in the art. Suitable human antibody preparations directed against CD34 and other cell surface markers on CD34+ cells may be obtained commercially from Cell Pro, Inc., Bothell, Wash., of Becton-Dickinson, Mountain View, Calif.

Suitable cell surface antigens on precursor cells include CD34 and other antigens on CD34+ cells, for example THY1, CD33, CD38, and CD74. The preferred cell surface marker is CD34. It is expected that the procedure will be successful using other cell surface antigens on CD34+ cells as markers for precursor cells.

Following a brief incubation of the sample with the antibody to enable binding, the precursor cell-antibody complex is recovered by any suitable method such as, for example, affinity chromatography, magnetic beads, and panning. In the preferred embodiment, recovery is by affinity chromatography. (See, e.g., R J Berenson et al. "Positive selection of viable cell populations using avidin-biotin immunoadsorption" J. Immunolog. Meth. 91, 11–19, 1986).

Briefly, the affinity recovery method utilizes a biotin-avidin coupling reaction in which the antibody is coupled to biotin by any suitable method. The antibody-biotin labeled precursor cell complex is separated from unbound materials by passing the reaction mixture through a column packed with an avidin labeled matrix. Unbound materials are removed from the column by washing. A useful commercially available cell separation kit includes biotin-labeled human anti-CD34 and a column packed with an avidin labeled matrix ("CEPRATE®LC" available from CellPro, Inc. Bothell, Wash.).

Indirect labeling methods are also within the scope of the invention. For example, the primary antibody could be directed against a precursor cell surface marker and a secondary antibody, labeled with biotin, directed against the primary antibody. Alternatively, the secondary antibody may be coupled to a suitable solid support material.

Negative selection schemes are also intended to be within the scope of the invention. Using a negative selection, the antibody, or other reagent, would be directed against a cell surface marker which is absent on CD34+ cells. The cells failing to bind to the reagent (i.e. antibody or lectin) are then isolated. In accordance with one embodiment a cell population enriched for cells having osteogenic and chondrogenic potential (i.e. cartilage and bone precursor cells) is prepared by contacting cells isolated from peripheral blood, bone marrow or adipose tissue with a reagent composition that binds to surface antigens not present on the surface of cartilage and bone precursor cells. The term "enriched cell population" is used in accordance with the present invention to designate a population of cells that have a higher percentage of a particular cell type relative to the percentage of that cell type in the natural tissue from which the cells were isolated. The reagent composition can be selected from lectins or antibodies that bind to cell surface antigens selected from the group consisting of CD3, CD8, CD10, CD15, CD19 and CD20. The CD3 and CD8 antigens are associated with T cells, the CD19 and CD20 antigens are associated with B cells, the CD15 antigen is associated with granulocytes, and the CD10 antigen is associated with lymphoid precursors and granulocytes. Preferably a combination of antibodies is utilized to bind several different antigens that are present on non progenitor cells. The cells not binding to the reagent composition are then recovered. Standard separation techniques, including chromatography, magnetic beads or panning, can be utilized to separate the cells that bind to the reagent from the cells that do not bind the reagent.

(b) Bone Marrow as the Source of Precursor Cells

The method disclosed above for isolating precursor cells from blood may be applied in essentially the same fashion to bone marrow. Bone marrow is collected by any suitable fashion, for example iliac crest aspiration. In the preferred embodiment the marrow is treated with an anticoagulant such as EDTA, heparin, or citrate and nucleated cells are separated from non-nucleated cells by any suitable means, for example by hemolysis or by density gradient centrifugation.

Precursor cells that express the CD34 cell surface antigen are isolated from marrow using a reagent that recognizes and binds to CD34 or to some other antigen on the surface of CD34+ cells. Suitable reagents include antibodies, lectins, and attachment molecules. Bound cells are separated from unbound cells by affinity chromatography, magnetic beads, or by panning.

In the preferred embodiment, an antibody directed against CD34 is used in the binding reaction and bound cells are separated from unbound cells by affinity chromatography, as disclosed more fully in the examples which follow.

(c) Adipose Tissue as the Source of Precursor Cells

As defined at the beginning of this section, adipose tissue" is used throughout this disclosure in a generic sense to mean fat and other tissue types (excluding connective tissues, hematologic tissues, periosteum, and perichondrium) which contain microvascular cells. Microvascular tissue, from which capillaries are made, is an integral part of the blood transport-system and, as such, is ubiquitous throughout the body. Microvascular tissue is composed of at least three cell types-endothelial, pericytes, and smooth muscle. Early investigations suggested that microvascular tissue might play an important role in bone metabolism. A key observation was that microvascular cells and tissue arose de novo and proliferated at sites of bone repair and new bone growth. Such observations led to speculation that endothelial cells, pericytes, or both may be osteoprecursor cells, or alternatively, that microvascular cells exert a mitogenic effect on bone precursor cells. (See e.g. C Brighton et al. "The pericyte as a possible osteoblast progenitor cell" Clin. Orthop. 275, 287–299, 1992) A more recent study using in vitro cultured cells suggests both progenitor-like cell proliferation and mitogenic effects; by microvascular cells. (A R Jones et al. "Microvessel endothelial cells and pericytes increase proliferation and repress osteoblast phenotype markers in rat calvarial bone cell cultures" J. Ortho. Res. 13, 553–561, 1995). Thus, within the microvascular cell population are precursor cells having osteogenic and chondrogenic potential.

The method of the present invention, as applied to adipose tissue, has two embodiments. In the first embodiment, the tissue is contacted with a reagent that recognizes CD34 or other surface antigen on CD34+ cells. As with peripheral blood and marrow, suitable binding reagents for use with adipose tissue include lectins, antibodies, and attachment molecules. The affinity binding method, as applied to adipose tissue, differs from the-method as applied to blood and marrow by requiring a step to produce a single-cell suspension before incubation with the antigen binding reagent. Any suitable dissociation enzyme such as, for example, collagenase may be used. Cells that bind the reagent can be removed from unbound cells by any suitable means, for example affinity chromatography, magnetic beads, or panning.

In the preferred embodiment of the invention as applied to adipose tissue, a sedimentation method is utilized to obtain a fraction of cells that is enriched for precursor cells having osteogenic and chondrogenic potential. Following harvest of the tissue and digestion with an enzyme to form a single-cell suspension, the cells are separated by gravity sedimentation on the bench top, or by centrifugation.

By way of example, fat could be secured by liposuction or any other suitable method. About 10 cc to 30 cc of fat tissue is digested with enough dissociation enzyme (e.g. collagenase) to produce a single-cell suspension. Suitable reaction conditions for enzyme digestion will vary depending on the enzyme used, as known to those skilled in the art. Following enzyme digestion, the adipocytes are separated from other cell types by centrifugation. Typically the cells are suspended in a buffered aqueous solution, wherein adipocytes float to the surface while denser cells having a density greater than 1.0 g/cm$^3$, which include precursor cells, collect on the bottom and are separable thereafter by any suitable means. After washing the harvested precursor cells they can be mixed with a suitable carrier and immediately implanted in vivo at a site needing repair.

II. In Vivo Mesenchymal Tissue Regeneration

The precursor cells recovered by the present procedure are useful for a variety of clinical applications. For example, they may be transplanted without further processing to a connective tissue site in a patient to promote the repair or regeneration of damaged bone or cartilage.

Unlike previous methods, the present invention does not require in vitro culturing in order to obtain a suitable cell type or an adequate quantity of precursor cells to be of use for in vivo application. The present invention takes advantage of the unexpected finding that osteogenic and chondrogenic precursor cells may be isolated from a variety of hematopoietic and non-hematopoietic body tissues such as peripheral blood and adipose tissue. This finding has created a heretofore unappreciated reservoir of precursor cells that can be drawn from conveniently to provide enough cells for in vivo applications without an additional time-consuming step of amplifying cell numbers by in vitro culturing. This aspect of the invention saves time and money with less risk of complication and pain for the patient.

By way of example only and in no way as a limitation on the invention, the precursor cells isolated by the present method from any suitable tissue source may be implanted at any connective tissue site needing bone or cartilage regeneration. Suitable implanting procedures include surgery or arthroscopic injection.

While the factors that determine biological differentiation are not fully understood, it is known that precursor cells will differentiate into bone or cartilage if transplanted to a site in the body needing repair. Precursor cells isolated by the present method can be implanted alone or premixed with bioactive compounds, for example, cell signaling molecules, including growth factors. Bioactive compounds suitable for use in accordance with the present invention include: transforming growth factor beta (TGFβ), bone morphogenic protein 2, 3, 4, or 7 (BMP 2, 3, 4, 7), basic fibroblast growth factor (bFGF), insulin-like growth factor I (IGF-I), sonic hedgehog (shh), indian hedgehog (ihh), growth and differentiation factors 5, 6, or 7 (GDF 5, 6, 7). Other cell signaling molecules suitable for use in accordance with the present invention include: vitronectin (VN), laminin (LN), bone sialoprotein (BSP), and osteopontin (OPN).

In accordance with one embodiment a method is provided for inducing the production of cartilage or bone at a predetermined site in need of repair. The method comprises the step of contacting the site with a composition comprising a population of cells enriched for cells having osteogenic and chondrogenic potential, wherein the cells are isolate from peripheral blood, bone marrow or adipose tissue. In one embodiment the population of cells is enriched in isolating progenitor cells is prepared based on the failure of progenitor cells to bind a reagent specific for a cell surface antigen selected from the group consisting of CD3, CD8, CD10, CD15, CD19 and CD20. Alternatively, the enriched population of cells is prepared by contacting a cell suspension prepared from peripheral blood, bone marrow or adipose tissue with a reagent that binds to cells bearing the CD34 antigen, to form a mixture of reagent bound cells and cells not bound to the reagent, and separating the reagent bound cells from the unbound cells using standard chromatography, magnetic beads or panning techniques.

In one preferred embodiment the cartilage or bone progenitor cells are combined with a biocompatible carrier material, well known to those skilled in the art, before the cells are surgically implanted or injected into a patient. The carrier functions to impede the dislodgement of the implanted cells and may also serve to further enhance the repair of the damaged or diseased tissue. Suitable carriers include but are not limited to, proteins such as collagen, gelatin, fibrin/fibrin clots, demineralized bone matrix (DBM), Matrigel® and Collastat®; carbohydrates such as starch, polysaccharides, saccharides, amylopectin, Hetastarch, alginate, methylcellulose and carboxymethylcellulose; proteoglycans, such as hyaluronate; agar; synthetic polymers; including polyesters (especially of normal metabolites such as glycolic acid, lactic acid, caprolactone, maleic acid, and glycols), polyethylene glycol, polyhydroxyethylmethacrylate, polymethylmethacrylate, poly(amino acids), polydioxanone, and polyanhydrides; ceramics, such as tricalcium phosphate, hydroxyapatite, alumina, zirconia, bone mineral and gypsum; glasses such as Bioglass, A-W glass, and calcium phosphate glasses; metals including titanium, Ti-6Al-4V, cobalt-chromium alloys, stainless steel and tantalum; and hydrogel matrices. In accordance with one embodiment the carrier is selected from a material that is biodegradable or bioresorbable.

The data presented in Table 2 demonstrate the operability of the invention for in vivo applications. The rat calvarial model used in these studies demonstrated that CD34+ cells isolated from marrow using a monoclonal antibody were as effective at promoting bone growth in an in vivo environment as were the positive controls (autologous graft). The data also show that the antibody itself can affect the outcome of the results probably via interaction with the complement system. For example, cells bound by mAb 5E6 did not stimulate bone growth in the rat calvarial model. Although both antibodies tested recognize CD34 and are IgM isotypes, 5E6 binds complement effectively while 2C6 does not.

III. Prosthetic Devices

A variety of clinically useful prosthetic devices have been developed for use in bone and cartilage grafting procedures. (see e.g. *Bone Grafts and Bone Substitutions*. Ed. M. B. Habal & A. H. Reddi, W. B. Saunders Co., 1992) For example, effective knee and hip replacement devices have been and continue to be widely used in the clinical environment. Many of these devices are fabricated using a variety of inorganic materials having low immunogenic activity, which safely function in the body. Examples of synthetic materials which have been tried and proven include titanium alloys, calcium phosphate, ceramic hydroxyapatite, and a variety of stainless steel and cobalt-chrome alloys. These materials provide structural support and can form a scaffolding into which host vascularization and cell migration can occur.

Although surface-textured prosthetic devices are effectively anchored into a host as bare inorganic structures, their attachment may be improved by seeding with osteogenic precursor cells, or bioactive compounds which attract and activate bone forming cells. Such "biological-seeding" is thought to enhance the effectiveness and speed with which attachment occurs by providing a fertile environment into which host vascularization and cell migration can occur.

The present invention provides a source of precursor cells which may be used to "seed" such prosthetic devices. In the preferred embodiment precursor cells are first mixed with a carrier material before application to a device. Suitable carriers well known to those skilled in the art include, but are not limited to, gelatin, fibrin, collagen, starch, polysaccharides, saccharides, proteoglycans, synthetic polymers, calcium phosphate, or ceramics. The carrier insures that the cells are retained on the porous surface of the implant device—for a useful time period.

Another related aspect of this invention is a kit useful for preparing prosthetic devices for bone and cartilage grafting procedures. The kit includes the one or more of a selection of biocompatible carriers and a reagent composition for preparing a population of cells enriched in progenitor cells from patient tissue. In one embodiment for producing a prosthesis from adipose tissue the kit comprises an enzyme mixture for producing a cell suspension from adipose tissue and a carrier matrix for combination with a population of cells enriched in progenitor cells derived from said cell suspension. The kit can also include buffers for use with the enzyme mixture and buffers for washing and handling the cell suspension. In one embodiment the kit can include disposable attachments for liposuction devices and disposable vessels for handling the isolated adipose tissue and cell suspension. The kit can also include a reagent composition that binds to cells bearing the CD34 antigen or a reagent composition that includes components binds to cells bearing an antigen selected from the group consisting of CD3, CD8, CD10, CD15, CD19 and CD20.

A more complete understanding of the present invention can be obtained by referring to the following illustrative examples of the practice of the invention, which examples are not intended, however, to be unduly limitative of the invention.

EXAMPLE 1

Animal Model for Bone Regenerating Capacity of Precursor Cells

A rat calvarial model was used to test the operability of the invention for in vivo applications. The model consisted of monitoring the ability of various test samples to promote bone growth in calvarial defects which had been surgically introduced into the rat skull. Calvarial defects were introduced into 6 month to 9 month old Fisher rats having bodyweights in the range of about 300 g to 500 g according to the following procedure. Animals were anesthetized by intramuscular injection using a Ketamine-Rompun (xylazine)-Acepromazine(acepromazine maleate) cocktail, and surgical incisions made in the calvarial portion of the skull. After peeling back the skin flap, a circular portion of the skull measuring 8 mm in diameter was removed using a drill with a circular trephine and saline irrigation. An 8 mm diameter disk of "GELFILM" was placed in each defect to separate the exposed brain from the test material and to maintain hemostasis. The calvarial defects produced in this fashion were then packed with a test sample consisting of an isolated cell population. For some experiments the test samples were mixed with a carrier material consisting of rat tail collagen or Avitene® bovine collagen before introduction into the calvarial defect. The positive control consisted of an autograft while the negative control consisted of a tricalcium phosphate (TCP) carrier only implant. After surgical closure of the wound site, treated animals were returned to their cages, maintained on a normal food and water regime, and sacrificed 28 days after surgery.

The effectiveness of a test sample to induce bone growth in calvarial defects was assessed by estimating new bone formation at the site of the defect by measuring the closure in the linear distance between cut bone edges or noting islands of bone growth in the central portion of the defect. The scoring criteria are shown in Table 1

TABLE 1

Bone Formation Scoring

| Site | Score | Description |
|---|---|---|
| Defect | 0 | No net gain in bone; either less formation than resorption or no formation at all. |
|  | 1 | Less that 5% of linear distance between cut bone edges is bridged by new bone. |
|  | 2 | About 5% to 33% of the defect is bridged by new bone, or there is an island of bone in the central portion of the defect. |
|  | 3 | About 33% to 66% of the defect is bridged by new bone. |
|  | 4 | Greater than 66% of the defect is bridged by new bone. |
|  | 5 | Complete bridging of the defect by new bone. |

TABLE 2

| Tissue/Cell Type | N | RBRA (Mean ± S.D.) |
|---|---|---|
| Autologous Graft (positive control) | 142 | 2.4 ± 0.7 |
| TCP (negative control) | 105 | 1.0 ± 0.9 |
| Marrow | 30 | 2.5 ± 1.1 |
| Marrow Ficoll | 18 | 2.3 ± 0.8 |
| Marrow/Avitene | 9 | 1.8 ± 0.4 |
| Blood Ficoll | 11 | 1.3 ± 0.5 |
| Blood/RTC Ficoll | 16 | 1.4 ± 0.5 |
| 2C6+ cells | 12 | 1.8 ± 0.4 |
| 2C6− cells | 12 | 0.7 ± 0.5 |
| 5E6+ cells | 12 | 1.3 ± 0.6 |
| 5E6− cells | 12 | 1.5 ± 0.5 |
| SBA+ cells | 12 | 1.8 ± 1.1 |
| SBA− cells | 18 | 1.4 ± 0.7 |

RBRA: Relative bone regeneration activity
N: Number of experiments
S.D.: Standard deviation
2C6 and 5E6 cells were isolated from marrow
SBA: Soy Bean Agglutinin The results are summarized in Table 2.

EXAMPLE 2

Isolation of an Enriched Nucleated Cell Population From Rat Bone Marrow

Rat bone marrow was isolated from the intramedullary cavities of 6 femurs taken from male Fisher rats between 8 to 10 weeks of age. Prior to sacrifice the animals had been maintained on a normal food and water diet. The marrow was extracted from excised femurs by flushing into a test tube containing approximately 5 ml of ACD buffer. Buffer ACD in the neat state consists of 2.2 g $Na_3Citrate.2H_2O$, 0.8 g citric acid, and 2.4 g dextrose dissolved in 100 ml distilled water. Unless otherwise noted, buffer ACD was diluted to a concentration of 15% in PBS. The extracted marrow cells were gently suspended into the buffer solution by pipetting. In order to separate red cells from white cells, the marrow cell suspension was underlaid with approximately 4 ml of Ficoll-Hypaque with a specific gravity of 1.09 (Sigma Chemical Co., St. Louis, Mo.) and centrifuged at 1200×g for 20 minutes. After centrifugation the interface layer containing the nucleated cells was removed by pipetting. The cells were washed in 5 ml of ACD and centrifuged at 250×g for 6 to 7 minutes. The pellet was washed twice more in 1% BSA/PBS (bovine serum albumin, phosphate buffered saline; supplied with CEPRATE LC kit). All PBS was $Ca^{+2}$ and $Mg^{+2}$ free to prevent clotting.

EXAMPLE 3

Isolation of CD34+ Cells From Rat Bone Marrow Using a Monoclonal Antibody and Affinity Chromatography and Their Use for In Vivo Bone Regeneration in Rat Calvarial Model Materials and Methods Mouse IgM monoclonal antibodies 2C6 and 5E6 were raised against rat CD34 present on the surface of a subpopulation of rat hematopoietic cells. The CD34 mAb's used in these experiments were the gift of Dr. Othmar Forster and were prepared in a manner well-known to those skilled in the art. Anti-mouse IgM:FITC, used for fluorescence sorting of cells bound with mAb's 2C6 and 5E6, was obtained from Boehringer Mannheim, Cat. # 100807. Avidin:FITC also used in fluorescence sorting was obtained from Boehringer Mannheim, Cat. # 100205. CD34+ cells labeled with mAb 2C6 or 5E6 were separated from unbound cells using an affinity column method. A useful, commercially available affinity cell separation kit, "CEPRATE LC," may be obtained from CellPro (CellPro, Inc. Bothell, Wash. 98021). Anti-mouse IgM:biotin was purchased from Southern Biotech, Birmingham, Ala., Cat. # 1022–08.

Cells carrying the CD34 surface antigen were isolated from rat marrow as follows. The rinsed nucleated cells, isolated in the manner described in Example 2, were resuspended in about 0.5 ml of 1% BSA/PBS (from CellPro kit). Then, a volume of mAb ranging in concentration from about 1 $\mu$g/ml to 40 $\mu$g/ml was added and the mixture incubated for about 1 hour at room temperature with occasional, gentle agitation. Following incubation the mixture was brought to 10 ml with 1% BSA/PBS and the mixture centrifuged at 250×g for 6 minutes. The pellet was gently resuspended and rinsed two additional times in 10 ml 1% BSA/PBS and spun as before. After another resuspension and centrifugation, the final cell pellet was resuspended in 2 ml 1% BSA/PBS for incubation with a biotinylated anti-mouse IgM.

About 10 $\mu$l of Goat anti-mouse IgM:biotin (0.5 mg/ml before dilution) was added to the resuspended mAb-cell pellet obtained at the previous step. The mixture was incubated at room temperature for about 30 minutes with gentle agitation, after which the cells were rinsed twice by centrifugation and resuspension in BSA/PBS, as previously described. The final cell pellet was resuspended to about 100×106 cells/ml in 5% BSA in a volume of 1 ml to 4 ml for loading onto an avidin column.

Antibody-labeled and unlabeled cells were separated on the "CEPRATE LC" avidin column using the conditions recommended by the manufacturer (Cell Pro, Inc., Bothell, Wash.). Briefly, the column contained a bed of PBS-equilibrated avidin matrix. Prior to loading the sample, about 5 ml of 5% BSA was run through the column. The pre-diluted cell sample was then layered onto the top of the gel matrix and the sample thereafter allowed to run into the matrix gel. Unlabeled cells were washed from the column with about 3 ml to 5 ml of PBS. The mAb-labeled cells were then released from the matrix and collected into a small volume of 5% BSA by gently squeezing the column so as to agitate the matrix while washing the column with PBS. Small aliquots were saved from the bound and unbound fractions for cell counting and flow cytometry. For implantation experiments the cells were washed 2 times in PBS/BSA and once in PBS only.

Results

Each experiment generated about 10 to 20×106 adherent cells of which about half this number were implanted into a calvarial defect. Cell fractions taken from the column were tested for Viability by trypan blue cell counts using a hemacytometer and found to be in the range of about 85% to 97% viable. The adherent cell population appeared to be a group of small blast cells. FACS was used to determine the purity of CD34+ cells isolated on the column. The adherent cell population contained about 50% of the original number of CD34+ cells at a purity of about 50%.

CD34+ cells were implanted into rat calvarial defects with or without a suitable carder material. Two carriers were tried in these experiments, Avitene bovine collagen and rat tail Collagen, both of which were found to be useful. Rat tail Collagen is preferred, however, since it showed the least inflammatory response. About 50 mg of Collagen was dissolved in 1 ml of PBS at 60° C. and equilibrated to 37° C. prior to mixing with cells. In some experiments pellets containing Collagen and cells were formed by mixing 100 pi of Collagen solution with a cell pellet and cooling the mixture to 4° C. prior to implantation into a calvarial defect. Surgical implantations were performed as described in Example 1 with sacrifice of recipient animals at 28 days post-surgery.

Histology scoring for bone formation was assessed according to the scheme shown in Table 1.

Discussion

The finding that CD34+ cells isolated by mAb 5E6 failed to stimulate bone regeneration in vivo may be explained by the ancillary observation that this antibody is a more effective activator of the complement system than mAb 2C6 (data not shown).

EXAMPLE 4

(a) Bone Regeneration in Rat Calvarial Model Using Ficoll-Separated Whole Blood

The rat calvarial model described in Example 1 was used to determine the bone regenerating capacity of Ficoll-separated whole blood. Approximately 2.5 ml of donor blood was used for each recipient calvarial defect. Donor animals were 8 to 10 week old male F344 strain rats. Recipients were 6 to 8 months old. Donors were bled into 3 cc syringes, which contained about 0.5 cc of ACD solution to inhibit coagulation.

| ACD Stock Solution | ACD Working Solution |
|---|---|
| 2.2 g Na3Citrate.2H2O | 15 ml ACD Stock Solution |
| 0.8 g citric acid. 1H2O | 100 ml PBS (Ca++/Mg++free) |
| 2.4 g dextrose | |
| 100 ml distilled water | |

Blood was placed into 15 ml conical tubes and brought up to 5 ml with ACD working solution. The samples were underlaid with 4 ml of Ficoll-Hypaque and centrifuged at 1200×g at room temperature for 20 minutes. After centrifugation, the white cell layer was removed from each tube by pipet.

Ficoll-separated blood cells were used for implantation experiments, either directly or after mixing with a carrier material. For direct implantation, the cell pellet was washed twice in 10 ml of PBS and the final pellet, containing roughly 5 to 10×10$^6$ cells, delivered neat into a calvarial defect. Cell samples pre-mixed with a carrier material were combined with rat tail collagen prior to implantation. About 50 mg of rat tail collagen (obtained from Sigma, St. Louis, Mo.; Cat. # C-8897) was heated to 60° C. in 500 μl PBS to dissolve the collagen protein. The collagen solution was equilibrated to 37° C. prior to mixing with the cell pellet. About 60 μl of collagen solution was mixed with the cell pellet and the entire cell-collagen mixture implanted into a calvarial defect.

EXAMPLE 5

Isolation of CD34+ Cells From Rat Blood Using a Monoclonal Antibody and Affinity Chromatography (1) Hemolysis Buffer—10×Stock Solution Dissolve the following in 1 L distilled water, adjust pH to 7.3, filter sterilize and store at 2–8° C.

83 g NH$_4$Cl
10 g NaHCO$_3$
4 g NA$_2$EDTA (2) Phosphate Buffered Saline (PBS) Ca2+ and M-g2+ Free Dissolve in 1 L distilled water, adjust pH to 7.2, filter sterilize, and store at 2–8° C.

8 g NaCl
1.15 g Na$_2$HPO$_4$
0.2 g KH$_3$PO$_4$
0.2 g KCl (3) PBS+Bovine Serum Albumin Dissolve 1 g BSA in 100 ml PBS.

(a) Approximately 100 ml of whole blood was collected by cardiac puncture from 17 male F344 rats 8 to 10 weeks old and heparinized by standard procedures. Red cells were lysed by mixing the whole blood with 300 ml of 1× hemolysis buffer at 37° C. and allowing the mixture to sit for about 3 minutes. Then 100 ml of PBS/BSA washing solution was added and the mixture centrifuged at 170×g for 10 minutes. The resulting supernatant was aspirated without disturbing the cell pellet. The pellet was washed two more times by gently resuspending in PBS/BSA followed by centrifugation. The final pellet was brought up to 2 ml in PBS/BSA in preparation for incubation with the mAb, and a small aliquot removed for cell counting and FACS analysis.

(b) The cell pellet, resuspended in 2 ml PBS/BSA as in step (a), was incubated with 3 ml of neat mAb 2C6 in order to bind CD34+ cells. The mAb-cell mixture was incubated at 4° C. for 45 minutes and the cells gently agitated once to resuspend during incubation. Following the incubation period the volume was brought up to 10 ml with PBS/BSA and the sample washed twice as in step (a). The washed pellet was resuspended in 2 ml PBS/BSA and 15 µl of goat anti-mouse IgM:biotin was added for a 30 minute incubation at 4° C. with one gentle agitation during incubation to resuspend cells. The cells were rinsed twice in PBS/BSA, as described in step (a), and the final pellet resuspended in 10 ml of 5% BSA. 5 ml of the resuspended pellet were used for each of two "CEPRATE LC" column sorts, as described in Example 3. Antibody-bound cells were released from the column as described in Example 3 and the released cells washed twice in PBS/BSA, and once in PBS. The final cell pellet was mixed on a glass slide with 60 µl of rat tail collagen (100 mg/ml) at 37° C., and the mixture of collagen and cells placed briefly on ice to form a solid pellet. The cell containing pellet was then transplanted immediately into a rat calvarial defect, as described in Example 1.

EXAMPLE 6

Isolation of Microvascular Cells From Rat Epididymal Fat Pads

Two epididymal fat pads were removed by dissection from a male Fisher F344 rat, minced with scissors under sterile conditions, and incubated in 10 ml PBS/1% BSA in the presence of 8 mg/ml collagenase (Type 11 Crude, 273 U/mg; Worthington Laboratories) for 45 minutes at 37° C. with gentle shaking. After digestion the sample was centrifuged at 250×g for 4 minutes and the low density fat at the top of the tube removed by aspiration. The pellet, which contained the precursor cells, was washed twice in PBS/1% BSA and once in PBS. The washed pellet was mixed with 50 µl rat tail collagen at 37° C., placed briefly on ice to gel, and implanted into a rat calvarial defect.

Sacrifice of recipient animals occurred at 28 days post surgery. Histology scoring for bone formation was assessed according to the scheme shown in Table 1. More new bone formation was observed in animals which received rat tail collagen including precursor cells (RBRA=2.0±0.4, n=80) than in animals which received carrier alone (RBRA=1.6±0.7, n=33). In a few examples, foci of cartilage were observed in the defects, though bone was more predominant. The presence of cartilage is unusual since it is not normally observed in skull defects, nor is it part of the normal remodeling process in this region.

EXAMPLE 7

Bone Formation In Vitro Using, Microvascular Endothelial Cells (1) Basic Cell Culture Media Combine, filter sterilize, and store at 2–8° C.

90 ml Dulbecco's Modified Eagle Medium (DMEM) (GIBCO Cat. 11885-076)

10 ml fetal bovine serum (heat inactivated) (Hyclone Cat. # A-1111-L)

1 ml L-glutamine (GIBCO Cat, # 15039-019)

(2) Culture Media Supplements (a) Endothelial cell growth supplement (ECGS)+Heparin (100× stock): Endothelial cell growth supplement (Sigma Cat # E-2759) 3.0 mg/ml in PBS Heparin (Sigma Cat. # H3149) 10,000 units/ml in PBS Aliquot 333 µl ECGS and 43.8 µl heparin/tube. Add one tube to 100 ml culture media.

(b) Dexamethasone (Dex)(Sigma Cat. #D-2915): Prepare $10^{-4}$ M concentrated stock in PBS. Add 10 µl to 100 ml media for final concentration of $10^{-8}$ M.

(c) L-Ascorbic Acid (ascorbate) (Sigma Cat # A-7631) Prepare 50 mg/ml solution in PBS. Add 100 µl to 100 ml media for final concentration of 50 µg/ml.

(d) β-glycerophosphate (Sigma Cat # G-9891) Prepare 200× stock of 2.16 g β-glycerophosphate to 10 ml PBS. Add 500 µl to 100 ml media for final concentration of 5 mM.

(3) Complete media formulations were composed of the basic cell culture media with one of the following three combinations of supplements.

(a) ECGS/heparin (b) ECGS/heparin+Dex+ascorbate (c) Dex+ascorbate

Each of the above media formulations was supplemented with β-glycerophosphate introduced at different time points in some experiments.

Methods

Microvascular endothelial cells were isolated from rat epididymal fat pads as described in Example 6. Following collagenase digestion and rinses, the cell pellet was resuspended in 20 ml of sterile 45% Percoll (Pharmacia) in PBS. The sample was divided into two sterile centrifuge tubes and spun at 13,000 RPM for 20 min at 10° C. The top band of cells was removed from the Percoll gradient by pipette. Cells were resuspended and rinsed twice in 0.1% BSA in PBS and once DMEM. The final cell pellet was resuspended in complete culture media and cells were plated into 6–10 gelatin coated T-25 flasks. Alternatively, cells were grown on collagen gels in T-25 flasks or petri dishes.

Collagen Gel Preparation 30 ml sterile rat tail collagen (Collaborative Cat # 40236)

3.4 ml PBS 340 ul 1N NaOH

Chill reagents and combine on ice. Quickly introduce 3–4 ml of mixture into each T-25 flask or 35 mm petri dish and harden to a gel at 37° C. for 30 min. before plating cells.

Cells were grown on both substrates in each of the three culture media formulations with three media changes per week. B-glycerophosphate was added to some cultures beginning at different time points and continued through the duration of the experiments.

Results

Cells which were supplemented with ECGS only grew the most quickly. Many adipocytes were present in the early days of the cultures. At later time points, tubule-like structures resembling those observed by others in endothelial cell primary cultures were observed. Though a few cell clusters were occasionally evident, cultures did not stain for mineralization using von Kossa or alizarin red staining procedures, or for cartilage using alcian blue or toluidine blue.

In contrast to those cultures which received the ECGS supplement, those which were placed in a traditional "mineralization" media containing dexamethasone and ascorbate exhibited a very different phenotype. These cultures grew slowly initially, but the predominant cell type was fibroblast-like. At one week, large numbers of rounded, though apparently metabolically active cells were present. By 2–3 weeks, cell clusters or nodules had formed within these cultures. These nodules resembled those observed in primary bone cultures of fetal rat calvariae. In 3–4 week cultures which received β-glycerophosphate, these nodules stained positively for calcium mineral by von Kossa and alizarin red.

Cultures which received both ECGS and Dex+ascorbate exhibited the widest range of phenotypes. Although some mineralized nodules were also evident in the cultures grown on the collagen gel substrate, cells tended to become quickly overgrown and fall off the gelatin coated plates.

EXAMPLE 9

Bone Formation Using Additional Carriers

Several additional carriers successfully induced new bone formation in the rat calvarial defect when combined with precursor cells derived from fat using the procedures described in Example 6.

(a) Demineralized bone matrix (DBM)

DBM was prepared from the long bones of Fisher (F344) rats by Osteotech (Shrewsbury, N.J.). DBM particles 250–425 μm in diameter were used in these studies. For each defect, approximately 5–10 mg of DBM was wetted with PBS then combined with the precursor cell pellet forming a paste-like slurry prior to transplantation. DBM with cells resulted in a RBRA of 3.20±0.63 (n=10).

(b) Microfibrillar collagen (Collastat® OBP)

For each calvarial defect, approximately 15–20 mg of hemostatic microfibrillar collagen (Collastat® OBP, Vitaphore Corporation) was combined with the final cell pellet in a small volume of PBS and gently kneaded into a putty-like material prior to implantation. RBRA with this treatment was 2.67±0.49 (n=12).

(c) Hyaluronan

Sodium hyaluronate gel (Orthovisc®, Anika Research, Inc.) was dispensed dropwise from the sterile packaging syringe onto the washed cell pellet and gently mixed with the cells. The approximate amount of hyaluronan per calvarial defect was 60–70 μl. RBRA was 2.25±0.45 (n=12).

(d) Exogenous fibrin clot

A mechanical method was used to produce fibrin clots directly from whole blood. In each experiment, 5 ml of blood was obtained from a donor Fisher (F344) rat via cardiac stick and placed immediately into a sterile tube. The blood was manually stirred in a circular motion with a roughened glass rod for 1–2 minutes until a clot formed around the rod. The rod was then touched to the side of the tube, twisted to remove excess blood cells and the final clot was gently slipped off and stored between sterile moistened gauze until transplantation. The resultant clot was a hollow 20–25 mm cylinder. Precursor cell pellets were pipetted directly into the center of the cylinder and each clot was used to fill two calvarial defects. RBRA with this treatment was 1.83±0.39 (n=12).

(e) Collagen gels

A modification of the in vitro collagen gel procedure described in Example 8 was used for the production of collagen gels which could be transplanted into the calvarial defect.

1.9 ml RTC 0.75 ml 4× DMEM (prepared from powder without phenol red)

0.35 ml sterile water 20 ul 1N NaOH

Cell pellets were gently stirred into chilled collagen gel reagents. 75 μl aliquots of the final mixture were placed into wells of a 96 well plate, incubated at 37° C. for 15 min., then covered with 75 μl of 1× DMEM and incubated an additional 15 min at 37° C. prior to implantation.

RBRA of precursor cells in Collagen gels was 1.92±0.29 (n=12). When the Percoll fraction of cells was used under the same experimental conditions, bone formation was slightly greater (RBRA=2.17±0.39, n=12).

(f) TCP

When TCP was combined directly with precursor cells and transplanted, RBRA was 1.44±0.62 (n=18). This effect was enhanced slightly by the addition of vitronectin or fibronectin to the implanted fraction (RBRA=1.67±0.49).

EXAMPLE 10

Bone Formation Using Attachment Molecules

Microvascular endothelial cells isolated from fat were isolated as described in Example 6. Rat tail collagen was prepared and held at 37° C. Immediately prior to mixing the collagen and cells, vitronectin (murine) (Gibco Cat. # 12174-017) was added directly into the rat tail collagen to a resulting concentration of 10 μg/ml. 60 μl of the RTC/vitronectin mixture was mixed with each cell pellet, chilled briefly on ice to harden, then transplanted into the calvarial defect resulting in a final concentration of 600 ng of vitronectin per implant. The concentration of vitronectin was the most useful of several doses tried.

Vitronectin in combination with precursor cells and a collagen carrier produced a significantly greater amount of bone (RBRA=2.08±0.29, n=12) than controls containing vitronectin and collagen alone (RBRA=1.67±0.65, n=12). Another interesting feature of the vitronectin experiments was the observation of large islands of bone growing under the Gelfilm separating the test article from the brain in the vitronectin treatments. This suggests that vitronectin might also serve in the recruitment of additional precursor cells to the defect site.

Experiments similar to those described with vitronectin were also performed using the fibronectin attachment molecule. Although some bone formation was observed with this molecule, significant differences were not seen between precursor cell groups and controls.

It is thought that the method for isolating and using bone and cartilage precursor cells by the present invention and many of its attendant advantages will be understood from the foregoing description and it will be apparent that various changes may be made in the form, construction, and arrangement of the elements thereof without departing from the spirit and scope of the invention or sacrificing all of its material advantages, the form hereinbefore described being merely a preferred or exemplary embodiment thereof.

We claim:

1. A method for inducing the production of cartilage or bone at a predetermined site in need of repair, said method comprising the step of contacting said site with a composition comprising a population of cells dissociated from adipose tissue said cell population enriched for cells having a density of at least 1.0 g/cm$^3$.

2. The method of claim 1 wherein the enriched cell population is cultured in vitro before contacting the site in need of repair.

3. The method of claim 1 wherein the site in need of repair is contacted with the population of cells by injecting said cells at the site in need of repair.

4. The method of claim 1 wherein the composition further comprises a biocompatible carrier.

5. The method of claim 1 wherein the composition further comprises a carrier selected from the group consisting of demineralized bone matrix, hyaluronate, Collastat®, polyesters, poly(amino acids), gypsum, fibrin, collagen, and calcium phosphate ceramics.

6. The method of claim 4 wherein the composition further comprises a bioactive compound.

7. A method of promoting the growth of bone or cartilage in a patient at a site in need of repair, said method comprising surgically implanting a prosthetic device at said site wherein the device comprises cells dissociated from adipose tissue and enriched for cells having a density of at least 1.0 $g/cm^3$.

8. The method of claim 7 wherein the enriched population of cells is generated by centrifugation or gravitational sedimentation of dissociated adipose tissue cells and isolation of cells having a density of at least 1.0 $g/cm^3$.

9. The method of claim 7 wherein the device further comprises a biocompatible carrier and vitronectin.

* * * * *